(12) United States Patent
Vind et al.

(10) Patent No.: US 7,919,298 B2
(45) Date of Patent: Apr. 5, 2011

(54) POLYPEPTIDES HAVING LIPASE ACTIVITY AND POLYNUCLEOTIDES ENCODING SAME

(75) Inventors: Jesper Vind, Vaerloese (DK); Jurgen Carsten Franz Knotzel, Copenhagen (DK); Kim Borch, Birkeroed (DK); Allan Svendsen, Hoersholm (DK); Thomas Hoenger Callisen, Frederiksberg C (DK); Debbie Yaver, Davis, CA (US); Mads Eskelund Bjoernvad, Virum (DK); Peter Kamp Hansen, Lejre (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/393,283

(22) Filed: Feb. 26, 2009

(65) Prior Publication Data
US 2009/0221033 A1  Sep. 3, 2009

Related U.S. Application Data

(60) Provisional application No. 61/032,443, filed on Feb. 29, 2008.

(30) Foreign Application Priority Data

Feb. 29, 2008 (EP) .................................. 08152163

(51) Int. Cl.
- C12N 9/20 (2006.01)
- C12N 1/20 (2006.01)
- C12N 15/00 (2006.01)
- C12Q 1/00 (2006.01)
- C12Q 1/68 (2006.01)
- C12P 21/04 (2006.01)
- C12P 7/00 (2006.01)
- C07H 21/04 (2006.01)

(52) U.S. Cl. ............. 435/198; 435/4; 435/6; 435/252.3; 435/320.1; 435/440; 435/69.1; 435/71.1; 435/132; 536/23.2

(58) Field of Classification Search ........................ None
See application file for complete search history.

(56) References Cited

U.S. PATENT DOCUMENTS

2005/0059130 A1 * 3/2005 Bojsen et al. ................. 435/198

FOREIGN PATENT DOCUMENTS

| | | |
|---|---|---|
| EP | 0 305 216 | 8/1988 |
| EP | 0 258 068 | 8/1994 |
| EP | 0 430 315 | 12/1997 |
| WO | WO 97/04079 | 2/1997 |
| WO | WO 97/07202 | 2/1997 |
| WO | WO 00/32758 | 6/2000 |
| WO | WO 00/60063 | 10/2000 |
| WO | WO 02/055679 | 7/2002 |
| WO | WO 02/062973 | 8/2002 |
| WO | WO 2007/087503 | 8/2007 |
| WO | WO 2007/087508 | 8/2007 |

OTHER PUBLICATIONS

Branden et al. Introduction to Protein Structure, Garland Publishing Inc., New York, p. 247, 1991.*

* cited by examiner

*Primary Examiner* — Yong D Pak
(74) *Attorney, Agent, or Firm* — Kristin J. McNamara

(57) ABSTRACT

The invention provides polypeptides obtained by introducing mutations in one or more regions identified in a parent lipase. The polypeptides of the present invention have surprisingly been found to have a low specific activity towards short chain fatty acids leading to a reduced odor generation and an increased BR over the lipases known in the art.

18 Claims, 3 Drawing Sheets

```
ID NO 1:    SSSSTQDYRIASEAEIKAHTFYTALSANA
ID NO 2:     SSSTQDYRIASEAEIKAHTFYTALSANA
ID NO 3:     SIDGGIRAATSQEINELTYYTTLSANS
ID NO 4:    SASDGGKVVAATTAQIQEFTKYAGIAATA
ID NO 5:        TAGHALAASTQ GISEDLYSRL VEMATISQAA
ID NO 6:        TAGHALAASTQ GISEDLYSRL VEMATISQAA
ID NO 7:          AVGVTTTDFSNFKFYIQHGAAA
ID NO 8:           TVTTQDLSNFRFYLQHADAA
ID NO 9:           DIPTTQLEDFKFWVQYAAAT
ID NO 10:          DVSTSELDQFEFWVQYAAAS
ID NO 11:          SVSTSTLDELQLFAQWSAAA
ID NO 12:          SVSTSTLDELQLFSQWSAAA
ID NO 13:          DVSSSLLNNLDLFAQYSAAA
ID NO 14:          EVSQDLFNQFNLFAQYSAAA
ID NO 15:        PQDAYTASHADLVKYATYAGLA

ID NO 1:    YCRTVIPG     GRWSCPHCGVAS   NLQITKTFST   LITDTNVLVAV
ID NO 2:    YCRTVIPG     GQWSCPHCDVAP   NLNITKTFTT   LITDTNVLVAV
ID NO 3:    YCRTVIPG     ATWDCIHCDATE   DLKIIKTWST   LIYDTNAMVAR
ID NO 4:    YCRSVVPG     NKWDCVQCQKWVP  DGKIITTFTS   LLSDTNGYVLR
ID NO 5:    YADLCNIPST                  IIKGEKIYNSQTDINGWILR
ID NO 6:    YADLCNIPST                  IIKGEKIYNSQTDINGWILR
ID NO 7:    YC   NSEAAA  GSKITCSNNGCPTVQGNGATIVTSF   VGSKTGIGGYVAT
ID NO 8:    YC   NFNTAV  GKPVHCSAGNCPDIEKDAAIVVGSV   VGTKTGIGAYVAT
ID NO 9:    YCPNNYVAKD   GEKLNCSVGNCPDVEAAGSTVKLSFS  DDTITDTAGFVAV
ID NO 10:   YYEADYTAQV   GDKLSCSKGNCPEVEATGATVSYDFS  DSTITDTAGYIAV
ID NO 11:   YCSNNID SK   DSNLTCTANACPSVEEASTTMLLEFDLTNDFGGTAGFLAA
ID NO 12:   YCSNNID SD   DSNVTCTADACPSVEEASTKMLLEFDLTNNFGGTAGFLAA
ID NO 13:   YCDENLN ST   GTKLTCSVGNCPLVEAASTQSLDEFNESSSYGNPAGYLAA
ID NO 14:   YCGKNNDAPA   GTNITCTGNACPEVEKADATFLYSFE  DSGVGDVTGFLAL
ID NO 15:   YQTTDAWPAS                  RTVPKDTTLISSFD  HTLKGSSGYIAF

ID NO 1:    GEKEKTIYVV  FRGTSSIRNA  IADIVFVPVN  YPPV    NGA  KVHKGFLDSY
ID NO 2:    GENEKTIYVV  FRGTSSIRNA  IADIVFVPVN  YPPV    NGA  KVHKGFLDSY
ID NO 3:    GDSEKTIYIV  FRGSSSIRNW  IADLTFVPVS  YPPV    SGT  KVHKGFLDSY
ID NO 4:    SDKQKTIYLV  FRGTNSFRSA  ITDIVFNFSD  YKPV    KGA  KVHAGFLSSY
ID NO 5:    DDSSKEIITV  FRGTGSDTNL  QLDTNYTLTP  FDTLPQCNGC  EVHGGYYIGW
ID NO 6:    DDSSKEIITV  FRGTGSDTNL  QLDTNYTLTP  FDTLPQCNSC  EVHGGYYIGW
ID NO 7:    DSARKEIVVS  FRGSINIRNW  LTNLDFG QE  DCSL    VSGC  GVHSGFQRAW
ID NO 8:    DNARKEIVVS  VRGSINVRNW  ITNFNFG QK  TCDL    VAGC  GVHTGFLDAW
ID NO 9:    DNTNKAIVVA  FRGSYSIRNW  VTDATFP QT  DPGL    CDGC  KAELGFWTAW
ID NO 10:   DHTNSAVVLA  FRGSYSVRNW  VADATFV HT  NPGL    CDGC  LAELGFWSSW
ID NO 11:   DNTNKRLVVA  FRGSSTIENW  IANLDFILED  NDDL    CTGC  KVHTGFWKAW
ID NO 12:   DNTNKRLVVA  FRGSSTIKNW  IADLDFILQD  NDDL    CTGC  KVHTGFWKAW
ID NO 13:   DETNKLLVLS  FRGSADLANW  VANLNFGLED  ASDL    CSGC  EVHSGFWKAW
ID NO 14:   DNTNKLIVLS  FRGSRSIENW  IGNLNFDLKE  INDI    CSGC  RGHDGFTSSW
ID NO 15:   NEPCKEIIVA  YRGTDSLIDW  LTNLNFDKTA  WPAN    ISNS  LVHEGFLNAY
```

Figure 1

| | | | | |
|---|---|---|---|---|
| ID NO 1: | NEVQDKLVAE | VKAQLDRHPG | YKIVVTGHSL | GGATAVLSALDLYHHGHA |
| ID NO 2: | NEVQDKLVAE | VKAQLDRHPG | YKIVVTGHSL | GGATAVLSALDLYHHGHD |
| ID NO 3: | GEVQNELVAT | VLDQFKQYPS | YKVAVTGHSL | GGATALLCALDLYQREEGLS |
| ID NO 4: | EQVVNDYFPV | VQEQLTAHPT | YKVIVTGHSL | GGAQALLAGMDLYQREPRLS |
| ID NO 5: | VSVQDQVESL | VKQQVSQYPD | YALTVTGHSL | GASLAALTAAQL SATYD |
| ID NO 6: | ISVQDQVESL | VQQQVSQFPD | YALTVTGHSL | GASLAALTAAQL SATYD |
| ID NO 7: | NEISSQATAA | VASARKANPS | FNVISTGHSL | GGAVAVLAAANLRVGGT |
| ID NO 8: | EEVAANVKAA | VSAAKTANPT | FKFVVTGHSL | GGAVATIAAAYLRKDGF |
| ID NO 9: | KVVRDRIIKT | LDELKPEHSD | YKIVVVGHSL | GAAIASLAAADLRTKNY |
| ID NO 10: | KLVRDDIIKE | LKEVVAQNPN | YELVVVGHSL | GAAVATLAATDLRGKGYP |
| ID NO 11: | ESAADELTSK | IKSAMSTYSG | YTLYFTGHSL | GGALATLGATVLRNDGY |
| ID NO 12: | EAAADNLTSK | IKSAMSTYSG | YTLYFTGHSL | GGALATLGATVLRNDGY |
| ID NO 13: | SEIADTITSK | VESALSDHSD | YSLVLTGHSY | GAALAALAATALRNSGH |
| ID NO 14: | RSVADTLRQK | VEDAVREHPD | YRVVFTGHSL | GGALATVAGADLRGNGY |
| ID NO 15: | LVSMQQVQEA | VDSLLAKCPD | ATISFTGHSL | GGALACISMVDTAQRHRGI |

| | | | | |
|---|---|---|---|---|
| ID NO 1: | NIEIYTQG | QPRIGTPAFA | NYVIGT | KIPYQRLVHERDIVPHL |
| ID NO 2: | NIEIYTQG | QPRIGTPEFA | NYVIGT | KIPYQRLVNERDIVPHL |
| ID NO 3: | SSNLFLYTQG | QPRVGDPAFA | NYVVST | GIPYRRTVNERDIVPHL |
| ID NO 4: | PKNLSIFTVG | GPRVGNPTFA | YYVEST | GIPFQRTVHKRDIVPHV |
| ID NO 5: | NIRLYTFG | EPRSGNQAFA | SYMNDAFQASSPDTTQYFRVTHANDGIPNL | |
| ID NO 6: | NIRLYTFG | EPRS NQAFA | SYMNDAFQASSPDTTQYFRVTHANDGIPNL | |
| ID NO 7: | PVDIYTYG | SPRVGNAQLS | AFVSNQ | AGGEYRVTHADDPVPRL |
| ID NO 8: | PFDLYTYG | SPRVGNDFFA | NFVTQQ | TGAEYRVTHGDDPVPRL |
| ID NO 9: | DAILYAYA | APRVANKPLA | EFITNQ | GNNYRFTHNDDPVPKL |
| ID NO 10: | SAKLYAYA | SPRVGNAALA | KYITAQ | GNNFRFTHTNDPVPKL |
| ID NO 11: | SVELYTYG | CPRIGNYALA | EHITSQ | GSGANFRVTHLNDIVPRV |
| ID NO 12: | SVELYTYG | CPRVGNYALA | EHITSQ | GSGANFPVTHLNDIVPRV |
| ID NO 13: | SVELYNYG | QPRLGNEALA | TYITDQ | NKGGNYRVTHTNDIVPKL |
| ID NO 14: | DIDVFSYG | APRVGNRAFA | EFLTVQ | TGGTLYRITHTNDIVPRL |
| ID NO 15: | KMQMFTYG | QPRTGNQAFA | EYVENL | GHPVFRVVYRHDIVPRM |

| | | | |
|---|---|---|---|
| ID NO 1: | PPGAFGFLHA | GEEFWIMK | DSSLRVCPNGIETDNCSNSIV |
| ID NO 2: | PPGAFGFLHA | GEEFWIMK | DSSLRVCPNGIETDNCSNSIV |
| ID NO 3: | PPAAFGFLHA | GEEYWITD | NSPETVQVCTSDLETSDCSNSIV |
| ID NO 4: | PPQSFGFLHP | GVESWIKS | GTSNVQICTSEIETKDCSNSIV |
| ID NO 5: | PPVEQGYAHG | GVEYWSV | DPYSAQNTFVCTGDEVQCCE AQGGQG |
| ID NO 6: | PPADEGYAHG | VVEYWSV | DPYSAQNTFVCTGDEVQCCE AQGGQG |
| ID NO 7: | PPLIFGYRHT | TPEFWLSGGGGDKVDYTISDVKVCEGAANLG CNGGTL | |
| ID NO 8: | PPIVFGYRHT | SPEYWLNG | GPLDKDYTVTEIKVCEGIANVM CNGGTI |
| ID NO 9: | PLLTMGYVHI | SPEYYITA | PDNTTVTDNQVTVLDGYVNFK GNTGTS |
| ID NO 10: | PLLSMGYVHV | SPEYWITS | PNNATVSTSDIKVIDGDVSFD GNTGTG |
| ID NO 11: | PPMDFGFSQP | SPEYWITS | GNGASVTASDIEVIEGINSTA GNAGEA |
| ID NO 12: | PPMDFGFSQP | SPEYWITS | GTGASVTASDIELIEGINSTA GNAGEA |
| ID NO 13: | PPTLLGYHHF | SPEYYISS | ADEATVTTTDVTEVTGIDATG GNDGTD |
| ID NO 14: | PPREFGYSHS | SPEYWIKS | GTLVPVTRNDIVKIEGIDATG GNNQPN |
| ID NO 15: | PPMDLGFQHH | GQEVWYEG | DENIKFCKGEGENLTCELGVP |

| | | | |
|---|---|---|---|
| ID NO 1: | PFT | SVIDHLSYLDMNTGL | CL |
| ID NO 2: | PFT | SVIDHLSYLDMNTGL | CL |
| ID NO 3: | PFT | SVLDHLSYFGINTGL | CT |
| ID NO 4: | PFT | SILDHLSYFDINEGS | CL |
| ID NO 5: | VN | NAHTTYF GMTSGACTW | |
| ID NO 6: | VN | NAHTTYF GMTSGHCTW | |

| | | |
|---|---|---|
| ID NO 7: | GL | DIAAHLYF QATDA CNAGGFSWR R |
| ID NO 8: | GL | DILAHITYF QSMAT CAPIAIPWK R |
| ID NO 9: | GGLPDLLAFHSHVWYFIHADACKGPGLPLR | |

Figure 1 (cont.)

```
ID NO 10:  LPLLTDFEAHIWYF VQVDA GKGPGLPFK R
ID NO 11:  TV    SVLAHLWYF FAISE CLL
ID NO 12:  TV    DVLAHLWYF FAISE CLL
ID NO 13:  GT    SIDAHRWYF IYISE CS
ID NO 14:  IP    DIPAHLWYF GLIGT CL
ID NO 15:  FSEL  NAKDHSEYP GMH
```

| ID NO: | Micro organism | SEQ ID NO.: |
|---|---|---|
| 1. | Absidia reflexa | 3 |
| 2. | Absidia corymbifera | 4 |
| 3. | Rhizmucor miehei | 5 |
| 4. | Rhizopus delemar (oryzea) | 6 |
| 5. | Aspergillus niger | 7 |
| 6. | Aspergillus tubingensis | 8 |
| 7. | Fusarium oxysporum | 9 |
| 8. | Fusarium heterosporum | 10 |
| 9. | Aspergillus oryzae | 11 |
| 10. | Penicilium camembertii | 12 |
| 11. | Aspergillus foetidus | 13 |
| 12 | Aspergillus niger | 14 |
| 13. | Aspergillus oryzea | 15 |
| 14. | Thermomyces lanuginosus | 2 |
| 15. | Landerina penisapora | 16 |

Figure 1. Alignment of lipase sequences.

Figure 1 (cont.)

SEQUENCE LISTING

```
<160> NUMBER OF SEQ ID NOS: 16

<210> SEQ ID NO 1
<211> LENGTH: 873
<212> TYPE: DNA
<213> ORGANISM: Thermomyces lanuginosus
<220> FEATURE:
<221> NAME/KEY: CDS
<222> LOCATION: (1)..(873)
<220> FEATURE:
<221> NAME/KEY: sig_peptide
<222> LOCATION: (1)..(51)
<220> FEATURE:
<221> NAME/KEY: propep
<222> LOCATION: (52)..(66)
<220> FEATURE:
<221> NAME/KEY: mat_peptide
<222> LOCATION: (67)..()

<400> SEQUENCE: 1 atg agg agc tcc ctt gtg ctg ttc ttt gtc tct gcg tgg acg gcc ttg        48
Met Arg Ser Ser Leu Val Leu Phe Phe Val Ser Ala Trp Thr Ala Leu
    -20              -15                  -10 gcc agt cct att cgt cga gag gtc tcg cag gat ctg ttt aac cag ttc        96
Ala Ser Pro Ile Arg Arg Glu Val Ser Gln Asp Leu Phe Asn Gln Phe
 -5               -1   1                   5                  10 aat ctc ttt gca cag tat tct gca gcc gca tac tgc gga aaa aac aat       144
Asn Leu Phe Ala Gln Tyr Ser Ala Ala Ala Tyr Cys Gly Lys Asn Asn
             15                  20                  25 gat gcc cca gct ggt aca aac att acg tgc acg gga aat gcc tgc ccc       192
Asp Ala Pro Ala Gly Thr Asn Ile Thr Cys Thr Gly Asn Ala Cys Pro
         30                  35                  40
```

```
gag gta gag aag gcg gat gca acg ttt ctc tac tcg ttt gaa gac tct       240
Glu Val Glu Lys Ala Asp Ala Thr Phe Leu Tyr Ser Phe Glu Asp Ser
         45                  50                  55 gga gtg ggc gat gtc acc ggc ttc ctt gct ctc gac aac acg aac aaa       288
Gly Val Gly Asp Val Thr Gly Phe Leu Ala Leu Asp Asn Thr Asn Lys
 60                  65                  70 ttg atc gtc ctc tct ttc cgt ggc tct cgt tcc ata gag aac tgg atc       336
Leu Ile Val Leu Ser Phe Arg Gly Ser Arg Ser Ile Glu Asn Trp Ile
 75                  80                  85                  90 ggg aat ctt aac ttc gac ttg aaa gaa ata aat gac att tgc tcc ggc       384
Gly Asn Leu Asn Phe Asp Leu Lys Glu Ile Asn Asp Ile Cys Ser Gly
                 95                 100                 105 tgc agg gga cat gac ggc ttc act tcg tcc tgg agg tct gta gcc gat       432
Cys Arg Gly His Asp Gly Phe Thr Ser Ser Trp Arg Ser Val Ala Asp
            110                 115                 120 acg tta agg cag aag gtg gag gat gct gtg agg gag cat ccc gac tat       480
Thr Leu Arg Gln Lys Val Glu Asp Ala Val Arg Glu His Pro Asp Tyr
        125                 130                 135 cgc gtg gtg ttt acc gga cat agc ttg ggt ggt gca ttg gca act gtt       528
Arg Val Val Phe Thr Gly His Ser Leu Gly Gly Ala Leu Ala Thr Val
    140                 145                 150 gcc gga gca gac ctg cgt gga aat ggg tat gat atc gac gtg ttt tca       576
Ala Gly Ala Asp Leu Arg Gly Asn Gly Tyr Asp Ile Asp Val Phe Ser
155                 160                 165                 170 tat ggc gcc ccc cga gtc gga aac agg gct ttt gca gaa ttc ctg acc       624
Tyr Gly Ala Pro Arg Val Gly Asn Arg Ala Phe Ala Glu Phe Leu Thr
                175                 180                 185 gta cag acc ggc gga aca ctc tac cgc att acc cac acc aat gat att       672
Val Gln Thr Gly Gly Thr Leu Tyr Arg Ile Thr His Thr Asn Asp Ile
            190                 195                 200 gtc cct aga ctc ccg ccg cgc gaa ttc ggt tac agc cat tct agc cca       720
Val Pro Arg Leu Pro Pro Arg Glu Phe Gly Tyr Ser His Ser Ser Pro
        205                 210                 215 gag tac tgg atc aaa tct gga acc ctt gtc ccc gtc acc cga aac gat       768
Glu Tyr Trp Ile Lys Ser Gly Thr Leu Val Pro Val Thr Arg Asn Asp
    220                 225                 230 atc gtg aag ata gaa ggc atc gat gcc acc ggc ggc aat aac cag cct       816
Ile Val Lys Ile Glu Gly Ile Asp Ala Thr Gly Gly Asn Asn Gln Pro
235                 240                 245                 250 aac att ccg gat atc cct gcg cac cta tgg tac ttc ggg tta att ggg       864
Asn Ile Pro Asp Ile Pro Ala His Leu Trp Tyr Phe Gly Leu Ile Gly
                255                 260                 265 aca tgt ctt                                                           873
Thr Cys Leu <210> SEQ ID NO 2
<211> LENGTH: 291
<212> TYPE: PRT
<213> ORGANISM: Thermomyces lanuginosus

<400> SEQUENCE: 2

Met Arg Ser Ser Leu Val Leu Phe Phe Val Ser Ala Trp Thr Ala Leu
            -20                 -15                 -10

Ala Ser Pro Ile Arg Arg Glu Val Ser Gln Asp Leu Phe Asn Gln Phe
         -5          -1   1               5                  10

Asn Leu Phe Ala Gln Tyr Ser Ala Ala Tyr Cys Gly Lys Asn Asn
                 15                  20                  25

Asp Ala Pro Ala Gly Thr Asn Ile Thr Cys Thr Gly Asn Ala Cys Pro
            30                  35                  40

Glu Val Glu Lys Ala Asp Ala Thr Phe Leu Tyr Ser Phe Glu Asp Ser
```

```
                45                  50                  55
Gly Val Gly Asp Val Thr Gly Phe Leu Ala Leu Asp Asn Thr Asn Lys
 60                  65                  70

Leu Ile Val Leu Ser Phe Arg Gly Ser Arg Ser Ile Glu Asn Trp Ile
 75                  80                  85                  90

Gly Asn Leu Asn Phe Asp Leu Lys Glu Ile Asn Asp Ile Cys Ser Gly
                 95                 100                 105

Cys Arg Gly His Asp Gly Phe Thr Ser Ser Trp Arg Ser Val Ala Asp
                110                 115                 120

Thr Leu Arg Gln Lys Val Glu Asp Ala Val Arg Glu His Pro Asp Tyr
                125                 130                 135

Arg Val Val Phe Thr Gly His Ser Leu Gly Gly Ala Leu Ala Thr Val
                140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
                190                 195                 200

Val Pro Arg Leu Pro Pro Arg Glu Phe Gly Tyr Ser His Ser Ser Pro
                205                 210                 215

Glu Tyr Trp Ile Lys Ser Gly Thr Leu Val Pro Val Thr Arg Asn Asp
                220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
                255                 260                 265

Thr Cys Leu

<210> SEQ ID NO 3
<211> LENGTH: 265
<212> TYPE: PRT
<213> ORGANISM: Absidia reflexa

<400> SEQUENCE: 3

Ser Ser Ser Ser Thr Gln Asp Tyr Arg Ile Ala Ser Glu Ala Glu Ile
 1               5                  10                  15

Lys Ala His Thr Phe Tyr Thr Ala Leu Ser Ala Asn Ala Tyr Cys Arg
                20                  25                  30

Thr Val Ile Pro Gly Gly Arg Trp Ser Cys Pro His Cys Gly Val Ala
                35                  40                  45

Ser Asn Leu Gln Ile Thr Lys Thr Phe Ser Thr Leu Ile Thr Asp Thr
 50                  55                  60

Asn Val Leu Val Ala Val Gly Glu Lys Glu Lys Thr Ile Tyr Val Val
 65                  70                  75                  80

Phe Arg Gly Thr Ser Ser Ile Arg Asn Ala Ile Ala Asp Ile Val Phe
                85                  90                  95

Val Pro Val Asn Tyr Pro Pro Val Asn Gly Ala Lys Val His Lys Gly
                100                 105                 110

Phe Leu Asp Ser Tyr Asn Glu Val Gln Asp Lys Leu Val Ala Glu Val
                115                 120                 125

Lys Ala Gln Leu Asp Arg His Pro Gly Tyr Lys Ile Val Val Thr Gly
                130                 135                 140

His Ser Leu Gly Gly Ala Thr Ala Val Leu Ser Ala Leu Asp Leu Tyr
145                 150                 155                 160
```

His His Gly His Ala Asn Ile Glu Ile Tyr Thr Gln Gly Gln Pro Arg
                165                 170                 175

Ile Gly Thr Pro Ala Phe Ala Asn Tyr Val Ile Gly Thr Lys Ile Pro
            180                 185                 190

Tyr Gln Arg Leu Val His Glu Arg Asp Ile Val Pro His Leu Pro Pro
        195                 200                 205

Gly Ala Phe Gly Phe Leu His Ala Gly Glu Glu Phe Trp Ile Met Lys
    210                 215                 220

Asp Ser Ser Leu Arg Val Cys Pro Asn Gly Ile Glu Thr Asp Asn Cys
225                 230                 235                 240

Ser Asn Ser Ile Val Pro Phe Thr Ser Val Ile Asp His Leu Ser Tyr
                245                 250                 255

Leu Asp Met Asn Thr Gly Leu Cys Leu
            260                 265

<210> SEQ ID NO 4
<211> LENGTH: 264
<212> TYPE: PRT
<213> ORGANISM: Absidia corymbifera

<400> SEQUENCE: 4

Ser Ser Ser Thr Gln Asp Tyr Arg Ile Ala Ser Glu Ala Glu Ile Lys
1               5                   10                  15

Ala His Thr Phe Tyr Thr Ala Leu Ser Ala Asn Ala Tyr Cys Arg Thr
            20                  25                  30

Val Ile Pro Gly Gly Gln Trp Ser Cys Pro His Cys Asp Val Ala Pro
        35                  40                  45

Asn Leu Asn Ile Thr Lys Thr Phe Thr Thr Leu Ile Thr Asp Thr Asn
    50                  55                  60

Val Leu Val Ala Val Gly Glu Asn Glu Lys Thr Ile Tyr Val Val Phe
65                  70                  75                  80

Arg Gly Thr Ser Ser Ile Arg Asn Ala Ile Ala Asp Ile Val Phe Val
                85                  90                  95

Pro Val Asn Tyr Pro Pro Val Asn Gly Ala Lys Val His Lys Gly Phe
            100                 105                 110

Leu Asp Ser Tyr Asn Glu Val Gln Asp Lys Leu Val Ala Glu Val Lys
        115                 120                 125

Ala Gln Leu Asp Arg His Pro Gly Tyr Lys Ile Val Val Thr Gly His
    130                 135                 140

Ser Leu Gly Gly Ala Thr Ala Val Leu Ser Ala Leu Asp Leu Tyr His
145                 150                 155                 160

His Gly His Asp Asn Ile Glu Ile Tyr Thr Gln Gly Gln Pro Arg Ile
                165                 170                 175

Gly Thr Pro Glu Phe Ala Asn Tyr Val Ile Gly Thr Lys Ile Pro Tyr
            180                 185                 190

Gln Arg Leu Val Asn Glu Arg Asp Ile Val Pro His Leu Pro Pro Gly
        195                 200                 205

Ala Phe Gly Phe Leu His Ala Gly Glu Glu Phe Trp Ile Met Lys Asp
    210                 215                 220

Ser Ser Leu Arg Val Cys Pro Asn Gly Ile Glu Thr Asp Asn Cys Ser
225                 230                 235                 240

Asn Ser Ile Val Pro Phe Thr Ser Val Ile Asp His Leu Ser Tyr Leu
                245                 250                 255

Asp Met Asn Thr Gly Leu Cys Leu
            260

<210> SEQ ID NO 5
<211> LENGTH: 269
<212> TYPE: PRT
<213> ORGANISM: Rhizomucor miehei

<400> SEQUENCE: 5

```
Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45

Leu Lys Ile Ile Lys Thr Trp Ser Thr Leu Ile Tyr Asp Thr Asn Ala
50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265
```

<210> SEQ ID NO 6
<211> LENGTH: 271
<212> TYPE: PRT
<213> ORGANISM: Rhizopus oryzae

<400> SEQUENCE: 6

```
Ser Ala Ser Asp Gly Gly Lys Val Val Ala Ala Thr Thr Ala Gln Ile
1               5                   10                  15

Gln Glu Phe Thr Lys Tyr Ala Gly Ile Ala Ala Thr Ala Tyr Cys Arg
            20                  25                  30

Ser Val Val Pro Gly Asn Lys Trp Asp Cys Val Gln Cys Gln Lys Trp
        35                  40                  45

Val Pro Asp Gly Lys Ile Ile Thr Thr Phe Thr Ser Leu Leu Ser Asp
50                  55                  60
```

```
Thr Asn Gly Tyr Val Leu Arg Ser Asp Lys Gln Lys Thr Ile Tyr Leu
 65                  70                  75                  80

Val Phe Arg Gly Thr Asn Ser Phe Arg Ser Ala Ile Thr Asp Ile Val
                 85                  90                  95

Phe Asn Phe Ser Asp Tyr Lys Pro Val Lys Gly Ala Lys Val His Ala
                100                 105                 110

Gly Phe Leu Ser Ser Tyr Glu Gln Val Val Asn Asp Tyr Phe Pro Val
                115                 120                 125

Val Gln Glu Gln Leu Thr Ala His Pro Thr Tyr Lys Val Ile Val Thr
                130                 135                 140

Gly His Ser Leu Gly Gly Ala Gln Ala Leu Leu Ala Gly Met Asp Leu
145                 150                 155                 160

Tyr Gln Arg Glu Pro Arg Leu Ser Pro Lys Asn Leu Ser Ile Phe Thr
                165                 170                 175

Val Gly Gly Pro Arg Val Gly Asn Pro Thr Phe Ala Tyr Tyr Val Glu
                180                 185                 190

Ser Thr Gly Ile Pro Phe Gln Arg Thr Val His Lys Arg Asp Ile Val
                195                 200                 205

Pro His Val Pro Pro Gln Ser Phe Gly Phe Leu His Pro Gly Val Glu
210                 215                 220

Ser Trp Ile Lys Ser Gly Thr Ser Asn Val Gln Ile Cys Thr Ser Glu
225                 230                 235                 240

Ile Glu Thr Lys Asp Cys Ser Asn Ser Ile Val Pro Phe Thr Ser Ile
                245                 250                 255

Leu Asp His Leu Ser Tyr Phe Asp Ile Asn Glu Gly Ser Cys Leu
                260                 265                 270

<210> SEQ ID NO 7
<211> LENGTH: 267
<212> TYPE: PRT
<213> ORGANISM: Aspergillus niger

<400> SEQUENCE: 7

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
                20                  25                  30

Ala Asp Leu Cys Asn Ile Pro Ser Thr Ile Ile Lys Gly Glu Lys Ile
                35                  40                  45

Tyr Asn Ser Gln Thr Asp Ile Asn Gly Trp Ile Leu Arg Asp Asp Ser
                50                  55                  60

Ser Lys Glu Ile Ile Thr Val Phe Arg Gly Thr Gly Ser Asp Thr Asn
 65                  70                  75                  80

Leu Gln Leu Asp Thr Asn Tyr Thr Leu Thr Pro Phe Asp Thr Leu Pro
                 85                  90                  95

Gln Cys Asn Gly Cys Glu Val His Gly Gly Tyr Tyr Ile Gly Trp Val
                100                 105                 110

Ser Val Gln Asp Gln Val Glu Ser Leu Val Lys Gln Gln Val Ser Gln
                115                 120                 125

Tyr Pro Asp Tyr Ala Leu Thr Val Thr Gly His Ser Leu Gly Ala Ser
                130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Gly Asn Gln Ala Phe Ala
                165                 170                 175
```

```
Ser Tyr Met Asn Asp Ala Phe Gln Ala Ser Ser Pro Asp Thr Thr Gln
            180                 185                 190

Tyr Phe Arg Val Thr His Ala Asn Asp Gly Ile Pro Asn Leu Pro Pro
        195                 200                 205

Val Glu Gln Gly Tyr Ala His Gly Gly Val Glu Tyr Trp Ser Val Asp
210                 215                 220

Pro Tyr Ser Ala Gln Asn Thr Phe Val Cys Thr Gly Asp Glu Val Gln
225                 230                 235                 240

Cys Cys Glu Ala Gln Gly Gly Gln Gly Val Asn Asn Ala His Thr Thr
                245                 250                 255

Tyr Phe Gly Met Thr Ser Gly Ala Cys Thr Trp
            260                 265

<210> SEQ ID NO 8
<211> LENGTH: 266
<212> TYPE: PRT
<213> ORGANISM: Aspergillus tubingensis

<400> SEQUENCE: 8

Thr Ala Gly His Ala Leu Ala Ala Ser Thr Gln Gly Ile Ser Glu Asp
1               5                   10                  15

Leu Tyr Ser Arg Leu Val Glu Met Ala Thr Ile Ser Gln Ala Ala Tyr
            20                  25                  30

Ala Asp Leu Cys Asn Ile Pro Ser Thr Ile Ile Lys Gly Glu Lys Ile
        35                  40                  45

Tyr Asn Ser Gln Thr Asp Ile Asn Gly Trp Ile Leu Arg Asp Asp Ser
50                  55                  60

Ser Lys Glu Ile Ile Thr Val Phe Arg Gly Thr Gly Ser Asp Thr Asn
65                  70                  75                  80

Leu Gln Leu Asp Thr Asn Tyr Thr Leu Thr Pro Phe Asp Thr Leu Pro
            85                  90                  95

Gln Cys Asn Ser Cys Glu Val His Gly Gly Tyr Tyr Ile Gly Trp Ile
        100                 105                 110

Ser Val Gln Asp Gln Val Glu Ser Leu Val Gln Gln Val Ser Gln
        115                 120                 125

Phe Pro Asp Tyr Ala Leu Thr Val Thr Gly His Ser Leu Gly Ala Ser
130                 135                 140

Leu Ala Ala Leu Thr Ala Ala Gln Leu Ser Ala Thr Tyr Asp Asn Ile
145                 150                 155                 160

Arg Leu Tyr Thr Phe Gly Glu Pro Arg Ser Asn Gln Ala Phe Ala Ser
            165                 170                 175

Tyr Met Asn Asp Ala Phe Gln Ala Ser Ser Pro Asp Thr Thr Gln Tyr
        180                 185                 190

Phe Arg Val Thr His Ala Asn Asp Gly Ile Pro Asn Leu Pro Pro Ala
    195                 200                 205

Asp Glu Gly Tyr Ala His Gly Val Val Glu Tyr Trp Ser Val Asp Pro
210                 215                 220

Tyr Ser Ala Gln Asn Thr Phe Val Cys Thr Gly Asp Glu Val Gln Cys
225                 230                 235                 240

Cys Glu Ala Gln Gly Gly Gln Gly Val Asn Asn Ala His Thr Thr Tyr
            245                 250                 255

Phe Gly Met Thr Ser Gly His Cys Thr Trp
        260                 265

<210> SEQ ID NO 9
<211> LENGTH: 276
```

<212> TYPE: PRT
<213> ORGANISM: Fusarium oxysporum

<400> SEQUENCE: 9

```
Ala Val Gly Val Thr Thr Thr Asp Phe Ser Asn Phe Lys Phe Tyr Ile
1               5                   10                  15

Gln His Gly Ala Ala Ala Tyr Cys Asn Ser Glu Ala Ala Ala Gly Ser
            20                  25                  30

Lys Ile Thr Cys Ser Asn Asn Gly Cys Pro Thr Val Gln Gly Asn Gly
        35                  40                  45

Ala Thr Ile Val Thr Ser Phe Val Gly Ser Lys Thr Gly Ile Gly Gly
    50                  55                  60

Tyr Val Ala Thr Asp Ser Ala Arg Lys Glu Ile Val Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
    130                 135                 140

Leu Gly Gly Ala Val Ala Val Leu Ala Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
        195                 200                 205

Gly Tyr Arg His Thr Thr Pro Glu Phe Trp Leu Ser Gly Gly Gly Gly
    210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
            260                 265                 270

Ser Trp Arg Arg
        275
```

<210> SEQ ID NO 10
<211> LENGTH: 273
<212> TYPE: PRT
<213> ORGANISM: Fusarium heterosporum

<400> SEQUENCE: 10

```
Thr Val Thr Thr Gln Asp Leu Ser Asn Phe Arg Phe Tyr Leu Gln His
1               5                   10                  15

Ala Asp Ala Ala Tyr Cys Asn Phe Asn Thr Ala Val Gly Lys Pro Val
            20                  25                  30

His Cys Ser Ala Gly Asn Cys Pro Asp Ile Glu Lys Asp Ala Ala Ile
        35                  40                  45

Val Val Gly Ser Val Val Gly Thr Lys Thr Ile Gly Ala Tyr Val
    50                  55                  60

Ala Thr Asp Asn Ala Arg Lys Glu Ile Val Val Ser Val Arg Gly Ser
```

```
                65                  70                  75                  80
Ile Asn Val Arg Asn Trp Ile Thr Asn Phe Asn Phe Gly Gln Lys Thr
                    85                  90                  95
Cys Asp Leu Val Ala Gly Cys Gly Val His Thr Gly Phe Leu Asp Ala
                100                 105                 110
Trp Glu Glu Val Ala Ala Asn Val Lys Ala Ala Val Ser Ala Ala Lys
            115                 120                 125
Thr Ala Asn Pro Thr Phe Lys Phe Val Val Thr Gly His Ser Leu Gly
        130                 135                 140
Gly Ala Val Ala Thr Ile Ala Ala Ala Tyr Leu Arg Lys Asp Gly Phe
145                 150                 155                 160
Pro Phe Asp Leu Tyr Thr Tyr Gly Ser Pro Arg Val Gly Asn Asp Phe
                165                 170                 175
Phe Ala Asn Phe Val Thr Gln Gln Thr Gly Ala Glu Tyr Arg Val Thr
                180                 185                 190
His Gly Asp Asp Pro Val Pro Arg Leu Pro Pro Ile Val Phe Gly Tyr
            195                 200                 205
Arg His Thr Ser Pro Glu Tyr Trp Leu Asn Gly Gly Pro Leu Asp Lys
        210                 215                 220
Asp Tyr Thr Val Thr Glu Ile Lys Val Cys Glu Gly Ile Ala Asn Val
225                 230                 235                 240
Met Cys Asn Gly Gly Thr Ile Gly Leu Asp Ile Leu Ala His Ile Thr
                245                 250                 255
Tyr Phe Gln Ser Met Ala Thr Cys Ala Pro Ile Ala Ile Pro Trp Lys
                260                 265                 270
Arg

<210> SEQ ID NO 11
<211> LENGTH: 278
<212> TYPE: PRT
<213> ORGANISM: Aspergillus oryzae

<400> SEQUENCE: 11

Asp Ile Pro Thr Thr Gln Leu Glu Asp Phe Lys Phe Trp Val Gln Tyr
1               5                   10                  15
Ala Ala Ala Thr Tyr Cys Pro Asn Asn Tyr Val Ala Lys Asp Gly Glu
                20                  25                  30
Lys Leu Asn Cys Ser Val Gly Asn Cys Pro Asp Val Glu Ala Ala Gly
            35                  40                  45
Ser Thr Val Lys Leu Ser Phe Ser Asp Asp Thr Ile Thr Asp Thr Ala
        50                  55                  60
Gly Phe Val Ala Val Asp Asn Thr Asn Lys Ala Ile Val Val Ala Phe
65                  70                  75                  80
Arg Gly Ser Tyr Ser Ile Arg Asn Trp Val Thr Asp Ala Thr Phe Pro
                85                  90                  95
Gln Thr Asp Pro Gly Leu Cys Asp Gly Cys Lys Ala Glu Leu Gly Phe
                100                 105                 110
Trp Thr Ala Trp Lys Val Val Arg Asp Arg Ile Ile Lys Thr Leu Asp
            115                 120                 125
Glu Leu Lys Pro Glu His Ser Asp Tyr Lys Ile Val Val Val Gly His
        130                 135                 140
Ser Leu Gly Ala Ala Ile Ala Ser Leu Ala Ala Ala Asp Leu Arg Thr
145                 150                 155                 160
Lys Asn Tyr Asp Ala Ile Leu Tyr Ala Tyr Ala Ala Pro Arg Val Ala
                165                 170                 175
```

```
Asn Lys Pro Leu Ala Glu Phe Ile Thr Asn Gln Gly Asn Asn Tyr Arg
            180                 185                 190

Phe Thr His Asn Asp Asp Pro Val Pro Lys Leu Pro Leu Leu Thr Met
            195                 200                 205

Gly Tyr Val His Ile Ser Pro Glu Tyr Tyr Ile Thr Ala Pro Asp Asn
            210                 215                 220

Thr Thr Val Thr Asp Asn Gln Val Thr Val Leu Asp Gly Tyr Val Asn
225                 230                 235                 240

Phe Lys Gly Asn Thr Gly Thr Ser Gly Gly Leu Pro Asp Leu Leu Ala
                245                 250                 255

Phe His Ser His Val Trp Tyr Phe Ile His Ala Asp Ala Cys Lys Gly
                260                 265                 270

Pro Gly Leu Pro Leu Arg
                275

<210> SEQ ID NO 12
<211> LENGTH: 278
<212> TYPE: PRT
<213> ORGANISM: Penicillium camemberti

<400> SEQUENCE: 12

Asp Val Ser Thr Ser Glu Leu Asp Gln Phe Glu Phe Trp Val Gln Tyr
1               5                   10                  15

Ala Ala Ala Ser Tyr Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
            35                  40                  45

Ala Thr Val Ser Tyr Asp Phe Ser Asp Ser Thr Ile Thr Asp Thr Ala
        50                  55                  60

Gly Tyr Ile Ala Val Asp His Thr Asn Ser Ala Val Val Leu Ala Phe
65                  70                  75                  80

Arg Gly Ser Tyr Ser Val Arg Asn Trp Val Ala Asp Ala Thr Phe Val
                85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
        115                 120                 125

Glu Val Val Ala Gln Asn Pro Asn Tyr Glu Leu Val Val Val Gly His
130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175

Gly Asn Ala Ala Leu Ala Lys Tyr Ile Thr Ala Gln Gly Asn Asn Phe
            180                 185                 190

Arg Phe Thr His Thr Asn Asp Pro Val Pro Lys Leu Pro Leu Leu Ser
        195                 200                 205

Met Gly Tyr Val His Val Ser Pro Glu Tyr Trp Ile Thr Ser Pro Asn
    210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
                260                 265                 270
```

Gly Leu Pro Phe Lys Arg
            275

<210> SEQ ID NO 13
<211> LENGTH: 270
<212> TYPE: PRT
<213> ORGANISM: Aspergillus foetidus

<400> SEQUENCE: 13

Ser Val Ser Thr Ser Thr Leu Asp Glu Leu Gln Leu Phe Ala Gln Trp
1               5                   10                  15

Ser Ala Ala Ala Tyr Cys Ser Asn Asn Ile Asp Ser Lys Asp Ser Asn
            20                  25                  30

Leu Thr Cys Thr Ala Asn Ala Cys Pro Ser Val Glu Glu Ala Ser Thr
        35                  40                  45

Thr Met Leu Leu Glu Phe Asp Leu Thr Asn Asp Phe Gly Gly Thr Ala
    50                  55                  60

Gly Phe Leu Ala Ala Asp Asn Thr Asn Lys Arg Leu Val Val Ala Phe
65                  70                  75                  80

Arg Gly Ser Ser Thr Ile Glu Asn Trp Ile Ala Asn Leu Asp Phe Ile
                85                  90                  95

Leu Glu Asp Asn Asp Asp Leu Cys Thr Gly Cys Lys Val His Thr Gly
            100                 105                 110

Phe Trp Lys Ala Trp Glu Ser Ala Ala Asp Glu Leu Thr Ser Lys Ile
        115                 120                 125

Lys Ser Ala Met Ser Thr Tyr Ser Gly Tyr Thr Leu Tyr Phe Thr Gly
    130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Ile
                165                 170                 175

Gly Asn Tyr Ala Leu Ala Glu His Ile Thr Ser Gln Gly Ser Gly Ala
            180                 185                 190

Asn Phe Arg Val Thr His Leu Asn Asp Ile Val Pro Arg Val Pro Pro
        195                 200                 205

Met Asp Phe Gly Phe Ser Gln Pro Ser Pro Glu Tyr Trp Ile Thr Ser
    210                 215                 220

Gly Asn Gly Ala Ser Val Thr Ala Ser Asp Ile Glu Val Ile Glu Gly
225                 230                 235                 240

Ile Asn Ser Thr Ala Gly Asn Ala Gly Glu Ala Thr Val Ser Val Leu
                245                 250                 255

Ala His Leu Trp Tyr Phe Phe Ala Ile Ser Glu Cys Leu Leu
            260                 265                 270

<210> SEQ ID NO 14
<211> LENGTH: 270
<212> TYPE: PRT
<213> ORGANISM: Aspergillus niger

<400> SEQUENCE: 14

Ser Val Ser Thr Ser Thr Leu Asp Glu Leu Gln Leu Phe Ser Gln Trp
1               5                   10                  15

Ser Ala Ala Ala Tyr Cys Ser Asn Asn Ile Asp Ser Asp Ser Asn
            20                  25                  30

Val Thr Cys Thr Ala Asp Ala Cys Pro Ser Val Glu Glu Ala Ser Thr
        35                  40                  45

```
Lys Met Leu Leu Glu Phe Asp Leu Thr Asn Asn Phe Gly Gly Thr Ala
 50                  55                  60

Gly Phe Leu Ala Ala Asp Asn Thr Asn Lys Arg Leu Val Val Ala Phe
 65                  70                  75                  80

Arg Gly Ser Ser Thr Ile Lys Asn Trp Ile Ala Asp Leu Asp Phe Ile
                 85                  90                  95

Leu Gln Asp Asn Asp Asp Leu Cys Thr Gly Cys Lys Val His Thr Gly
                100                 105                 110

Phe Trp Lys Ala Trp Glu Ala Ala Asp Asn Leu Thr Ser Lys Ile
                115                 120                 125

Lys Ser Ala Met Ser Thr Tyr Ser Gly Tyr Leu Tyr Phe Thr Gly
                130                 135                 140

His Ser Leu Gly Gly Ala Leu Ala Thr Leu Gly Ala Thr Val Leu Arg
145                 150                 155                 160

Asn Asp Gly Tyr Ser Val Glu Leu Tyr Thr Tyr Gly Cys Pro Arg Val
                165                 170                 175

Gly Asn Tyr Ala Leu Ala Glu His Ile Thr Ser Gln Gly Ser Gly Ala
                180                 185                 190

Asn Phe Pro Val Thr His Leu Asn Asp Ile Val Pro Arg Val Pro Pro
                195                 200                 205

Met Asp Phe Gly Phe Ser Gln Pro Ser Pro Glu Tyr Trp Ile Thr Ser
                210                 215                 220

Gly Thr Gly Ala Ser Val Thr Ala Ser Asp Ile Glu Leu Ile Glu Gly
225                 230                 235                 240

Ile Asn Ser Thr Ala Gly Asn Ala Gly Glu Ala Thr Val Asp Val Leu
                245                 250                 255

Ala His Leu Trp Tyr Phe Phe Ala Ile Ser Glu Cys Leu Leu
                260                 265                 270

<210> SEQ ID NO 15
<211> LENGTH: 269
<212> TYPE: PRT
<213> ORGANISM: Aspergillus oryzae

<400> SEQUENCE: 15

Asp Val Ser Ser Leu Leu Asn Asn Leu Asp Leu Phe Ala Gln Tyr
 1               5                  10                  15

Ser Ala Ala Ala Tyr Cys Asp Glu Asn Leu Asn Ser Thr Gly Thr Lys
                 20                  25                  30

Leu Thr Cys Ser Val Gly Asn Cys Pro Leu Val Glu Ala Ala Ser Thr
                 35                  40                  45

Gln Ser Leu Asp Glu Phe Asn Glu Ser Ser Tyr Gly Asn Pro Ala
 50                  55                  60

Gly Tyr Leu Ala Ala Asp Glu Thr Asn Lys Leu Leu Val Leu Ser Phe
 65                  70                  75                  80

Arg Gly Ser Ala Asp Leu Ala Asn Trp Val Ala Asn Leu Asn Phe Gly
                 85                  90                  95

Leu Glu Asp Ala Ser Asp Leu Cys Ser Gly Cys Glu Val His Ser Gly
                100                 105                 110

Phe Trp Lys Ala Trp Ser Glu Ile Ala Asp Thr Ile Thr Ser Lys Val
                115                 120                 125

Glu Ser Ala Leu Ser Asp His Ser Asp Tyr Ser Leu Val Leu Thr Gly
                130                 135                 140

His Ser Tyr Gly Ala Ala Leu Ala Ala Leu Ala Ala Thr Ala Leu Arg
145                 150                 155                 160
```

Asn Ser Gly His Ser Val Glu Leu Tyr Asn Tyr Gly Gln Pro Arg Leu
            165                 170                 175

Gly Asn Glu Ala Leu Ala Thr Tyr Ile Thr Asp Gln Asn Lys Gly Gly
            180                 185                 190

Asn Tyr Arg Val Thr His Thr Asn Asp Ile Val Pro Lys Leu Pro Pro
            195                 200                 205

Thr Leu Leu Gly Tyr His His Phe Ser Pro Glu Tyr Tyr Ile Ser Ser
210                 215                 220

Ala Asp Glu Ala Thr Val Thr Thr Thr Asp Val Thr Glu Val Thr Gly
225                 230                 235                 240

Ile Asp Ala Thr Gly Gly Asn Asp Gly Thr Asp Gly Thr Gly Ser Ile Asp
            245                 250                 255

Ala His Arg Trp Tyr Phe Ile Tyr Ile Ser Glu Cys Ser
            260                 265

<210> SEQ ID NO 16
<211> LENGTH: 251
<212> TYPE: PRT
<213> ORGANISM: Landerina penisapora

<400> SEQUENCE: 16

Pro Gln Asp Ala Tyr Thr Ala Ser His Ala Asp Leu Val Lys Tyr Ala
1               5                   10                  15

Thr Tyr Ala Gly Leu Ala Tyr Gln Thr Thr Asp Ala Trp Pro Ala Ser
            20                  25                  30

Arg Thr Val Pro Lys Asp Thr Thr Leu Ile Ser Ser Phe Asp His Thr
            35                  40                  45

Leu Lys Gly Ser Ser Gly Tyr Ile Ala Phe Asn Glu Pro Cys Lys Glu
50                  55                  60

Ile Ile Val Ala Tyr Arg Gly Thr Asp Ser Leu Ile Asp Trp Leu Thr
65                  70                  75                  80

Asn Leu Asn Phe Asp Lys Thr Ala Trp Pro Ala Asn Ile Ser Asn Ser
            85                  90                  95

Leu Val His Glu Gly Phe Leu Asn Ala Tyr Leu Val Ser Met Gln Gln
            100                 105                 110

Val Gln Glu Ala Val Asp Ser Leu Leu Ala Lys Cys Pro Asp Ala Thr
            115                 120                 125

Ile Ser Phe Thr Gly His Ser Leu Gly Gly Ala Leu Ala Cys Ile Ser
130                 135                 140

Met Val Asp Thr Ala Gln Arg His Arg Gly Ile Lys Met Gln Met Phe
145                 150                 155                 160

Thr Tyr Gly Gln Pro Arg Thr Gly Asn Gln Ala Phe Ala Glu Tyr Val
            165                 170                 175

Glu Asn Leu Gly His Pro Val Phe Arg Val Val Tyr Arg His Asp Ile
            180                 185                 190

Val Pro Arg Met Pro Pro Met Asp Leu Gly Phe Gln His His Gly Gln
            195                 200                 205

Glu Val Trp Tyr Glu Gly Asp Glu Asn Ile Lys Phe Cys Lys Gly Glu
            210                 215                 220

Gly Glu Asn Leu Thr Cys Glu Leu Gly Val Pro Phe Ser Glu Leu Asn
225                 230                 235                 240

Ala Lys Asp His Ser Glu Tyr Pro Gly Met His
            245                 250

POLYPEPTIDES HAVING LIPASE ACTIVITY AND POLYNUCLEOTIDES ENCODING SAME

CROSS-REFERENCE TO RELATED APPLICATIONS

This application claims priority or the benefit under 35 U.S.C. 119 of European application no. 08152163.5 filed Feb. 29, 2008 and U.S. provisional application No. 61/032,443 filed Feb. 29, 2008, the contents of which are fully incorporated herein by reference.

FIELD OF THE INVENTION

The present invention relates to lipase variants with an improved wash effect to odor generation and to a method of preparing them. It particularly relates to variants of the *Thermomyces lanuginosus* lipase.

SEQUENCE LISTING

The present application contains a computer-readable form of a sequence listing, which is fully incorporated herein by reference.

BACKGROUND OF THE INVENTION

Lipases are useful, e.g., as detergent enzymes to remove lipid or fatty stains from clothes and other textiles, and as additives to dough for bread and other baked products. Thus, a lipase derived from *Thermomyces lanuginosus* (synonym *Humicola lanuginosa*, EP 258068 and EP 305216) is sold for detergent use under the trade name Lipolase® (product of Novozymes A/S). WO 0060063 describes variants of the *T. lanuginosus* lipase with a particularly good first-wash performance in a detergent solution. WO 9704079, WO 9707202 and WO 0032758 also disclose variants of the *T. lanuginosus* lipase.

In some applications, it is of interest to minimize the formation of odor-generating short-chain fatty acids. Thus, it is known that laundry detergents with lipases may sometimes leave residual odors attached to cloth soiled with milk (EP 430315). WO 02062973 discloses lipase variants where the odor generation has been reduced by attaching a C-terminal extension. The recently published WO 07087508 discloses lipase variants where the odor generation has been reduced by introducing mutations in one or more regions identified in a parent lipase. WO 07087503 describes polypeptides having lipase activity and which further has a RP of at least 0.8 and a BR of at least 1.1 at the test conditions given in the specification.

SUMMARY OF THE INVENTION

In a first aspect, the invention relates to a first polypeptide having lipase activity wherein said polypeptide is a polypeptide having at least one of: (a) a lipase activity (LU) relative to the absorbance at 280 nm (A280) of less than 500 LU/A280, in which one unit of LU (1 LU) is defined as the amount of enzyme capable of releasing 1 micro mol of butyric acid per minute at 30° C. at pH 7, and the absorbance of the polypeptide is measured at 280 nm; (b) a Risk performance odor (R) below 0.5, in which R is calculated as the ratio between the amount butyric acid released from a polypeptide washed swatch and the amount butyric acid released from a reference polypeptide washed swatch, after both values have been corrected for the amount of butyric acid released from a non-polypeptide washed swatch; or (c) a Benefit Risk factor (BR) of at least 1.8, in which BR is defined as the average wash performance ($RP_{avg}$) divided with the risk performance odor (R).

In a second aspect, the invention relates to a second polypeptide having lipase activity comprising alterations of the amino acids at the positions T231R+N233R+I255A+P256K and at least one of (a) S58A+V60S+A150G+L227G; or (b) E210V/G; which positions are corresponding to SEQ ID NO: 2.

In further aspects, the invention relates to an isolated polynucleotide encoding the polypeptide having lipase activity, a nucleic acid construct comprising the polynucleotide, a recombinant expression vector comprising the nucleic acid construct, and a transformed host cell comprising the nucleic acid construct or the recombinant expression vector.

In a further aspect, the invention relates to a method of preparing the polypeptide comprising the steps: (a) cultivating the transformed host cell comprising the nucleic acid construct or the recombinant expression vector comprising the polypeptide under conditions conductive for the production of the polypeptide; and (b) recovering the polypeptide.

In a further aspect, the invention relates to a formulation comprising the polypeptide.

In a further aspect, the invention relates to a method of reducing the formation of odor generating short chain fatty acids during lipid hydrolysis by employing the polypeptide.

BRIEF DESCRIPTION OF THE FIGURES

FIG. 1 shows the alignment of lipases.

SEQUENCE LISTINGS

SEQ ID NO: 1 shows the DNA sequence encoding lipase from *Thermomyces lanoginosus*.
SEQ ID NO: 2 shows the amino acid sequence of a lipase from *Thermomyces lanoginosus*.
SEQ ID NO: 3 shows the amino acid sequence of a lipase from *Absidia reflexa*.
SEQ ID NO: 4 shows the amino acid sequence of a lipase from *Absidia corymbifera*.
SEQ ID NO: 5 shows the amino acid sequence of a lipase from *Rhizomucor miehei*.
SEQ ID NO: 6 shows the amino acid sequence of a lipase from *Rhizopus oryzae*.
SEQ ID NO: 7 shows the amino acid sequence of a lipase from *Aspergillus niger*.
SEQ ID NO: 8 shows the amino acid sequence of a lipase from *Aspergillus tubingensis*.
SEQ ID NO: 9 shows the amino acid sequence of a lipase from *Fusarium oxysporrum*.
SEQ ID NO: 10 shows the amino acid sequence of a lipase from *Fusarium heterosporum*.
SEQ ID NO: 11 shows the amino acid sequence of a lipase from *Aspergillus oryzae*.
SEQ ID NO: 12 shows the amino acid sequence of a lipase from *Penicillium camemberti*.
SEQ ID NO: 13 shows the amino acid sequence of a lipase from *Aspergillus foetidus*.
SEQ ID NO: 14 shows the amino acid sequence of a lipase from *Aspergillus niger*.
SEQ ID NO: 15 shows the amino acid sequence of a lipase from *Aspergillus oryzae*.
SEQ ID NO: 16 shows the amino acid sequence of a lipase from *Landerina penisapora*.

DETAILED DESCRIPTION OF THE INVENTION

Use of lipases to remove lipid and fatty stains is known in the art where the activities of lipases that result in release of free short chain lipids, such as e.g. butyric acid are associated with an undesirable odor. Hydrolysis of the substrate tributyrin results in the release of butyric acid. The polypeptides of the present invention have surprisingly been found to have a low specific activity, measured as LU/A280; towards tributyrin at neutral pH cf. example 2 and table 3.

The Benefit Risk factor (BR) is calculated by dividing the relative (wash) performance (benefit, RP) with the risk performance odor (risk, R). The wash performance may be measured by an automated mechanical stress assay (AMSA) cf. example 3, and the odor generation may be measured directly by gas chromatography, cf. example 4 and table 3. A reduced odor affects the BR and may lead to an increase in BR. The polypeptides of the present invention have furthermore been found to have a reduced odor generation and an increased BR over the lipases known in the art cf. example 5 and table 3.

Lipase activity (LU): The term "lipase activity" as used herein means a carboxylic ester hydrolase activity which catalyses the hydrolysis of triacylglycerol under the formation of diacylglycerol and a carboxylate. For the purpose of the present invention, lipase activity is determined according to the following procedure: A substrate for lipase is prepared by emulsifying tributyrin (glycerin tributyrate) using gum Arabic as emulsifier. The hydrolysis of tributyrin at 30° C. at pH 7 or 9 is followed in a pH-stat titration experiment. One unit of lipase activity (1 LU) is defined as the amount of enzyme capable of releasing 1 micro mol of butyric acid per minute at 30° C., pH 7.

Risk performance odor (R): The term "risk performance odor" as used herein means the ratio between the amount butyric acid released from a polypeptide washed swatch and the amount butyric acid released from a reference polypeptide washed swatch, after both values have been corrected for the amount of butyric acid released from a non-polypeptide washed swatch.

Relative performance (RP): The term "relative performance" as used herein means the wash performance of the polypeptide compared to the wash performance of a reference polypeptide. For the purpose of the present invention, relative performance is determined according to the procedure described in example 3.

Reference polypeptide: The term "reference polypeptide", "reference enzyme" or "reference lipase" as used herein means the mature part of SEQ ID NO: 2 with the substitutions T231R+N233R.

Benefit Risk factor (BR): The term "Benefit Risk factor" as used herein means the average relative performance ($RP_{avg}$) compared to the risk for odor generation (R) and has the following formula: $BR=RP_{avg}/R$.

Nomenclature for Amino Acid Modifications

In describing lipase variants according to the invention, the following nomenclature is used for ease of reference:

Original amino acid(s):position(s):substituted amino acid(s)

According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific lipase contains a "deletion" in comparison with other lipases and an insertion is made in such a position this is indicated as *36D for insertion of an aspartic acid in position 36.

Multiple mutations are separated by pluses, i.e.: R170Y+ G195E, representing mutations in positions 170 and 195 substituting tyrosine and glutamic acid for arginine and glycine, respectively.

X231 indicates the amino acid in a parent polypeptide corresponding to position 231, when applying the described alignment procedure. X231R indicates that the amino acid is replaced with R. For SEQ ID NO: 2 X is T, and X231R thus indicates a substitution of T in position 231 with R. Where the amino acid in a position (e.g. 231) may be substituted by another amino acid selected from a group of amino acids, e.g. the group consisting of R and P and Y, this will be indicated by X231R/P/Y.

In all cases, the accepted IUPAC single letter or triple letter amino acid abbreviation is employed.

Identity: The term "identity" as used herein means the relatedness between two amino acid sequences or between two nucleotide sequences is described by the parameter "identity".

For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.

The degree of identity between an amino acid sequence of the present invention ("invention sequence"; e.g. amino acids 1 to 269 of SEQ ID NO: 2) and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

An exact match occurs when the "invention sequence" and the "foreign sequence" have identical amino acid residues in the same positions of the overlap. The length of a sequence is the number of amino acid residues in the sequence (e.g. the length of SEQ ID NO: 2 are 269).

The above procedure may be used for calculation of identity as well as homology and for alignment. In the context of the present invention homology and alignment has been calculated as described below.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

In the present invention, corresponding (or homologous) positions in the lipase sequences of *Absidia reflexa, Absidia corymbefera, Rhizmucor miehei, Rhizopus delemar, Aspergillus niger, Aspergillus tubigensis, Fusarium oxysporum, Fusarium heterosporum, Aspergillus oryzea, Penicilium camembertii, Aspergillus foetidus, Aspergillus niger, Thermomyces lanoginosus* (synonym: *Humicola lanuginose*) and *Landerina penisapora* are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

Sources of Polypeptides Having Lipase Activity

Any suitable polypeptide may be used. In some embodiments the polypeptide may be a fungal polypeptide.

The polypeptide may be a yeast polypeptide originating from genera such as a *Candida, Kluyveromyces, Pichia, Saccharomyces, Schizosaccharomyces,* or *Yarrowia*; or more preferably a filamentous fungal polypeptide originating from genera such as a *Acremonium, Aspergillus, Aureobasidium, Cryptococcus, Filobasidium, Fusarium, Humicola, Magnaporthe, Mucor, Myceliophthora, Neocallimastix, Neurospora, Paecilomyces, Penicllium, Piromyces, Schizophyllum, Talaromyces, Thermoascus, Thielavia, Tolypocladium, Thermomyces* or *Trichoderma.*

The polypeptide may furthermore be a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having lipase activity.

Alternatively, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Aspergillus turbigensis, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Thermomyces lanoginosus* (synonym: *Humicola lanuginose), Mucor miehei, Myceliophthora thermophila, Neurospora crassa, Penicillium purpurogenum, Trichoderma harzianum, Trichoderma koningii, Trichoderma longibrachiatum, Trichoderma reesei,* or *Trichoderma viride* polypeptide.

In some embodiments the invention relates to a polypeptide which is a *Thermomyces* lipase.

In some embodiments the invention relates to a polypeptide which is a *Thermomyces lanuginosus* lipase.

In some embodiments the invention relates to a polypeptide, wherein the polypeptide is at least 50%, at least 60%, at least 70%, at least 80%, at least 85%, at least 90%, at least 95%, at least 96%, at least 97%, at least 98%, at least 99% or 100% identical to SEQ ID NO: 2.

Identification of Alterations in Polypeptides Having Lipase Activity

The positions referred to below are the positions of the amino acid residues in SEQ ID NO: 2. The procedure described in the paragraph "Homology and alignment" is used to find the corresponding or homologous position of the amino acid residue in a different lipase.

In some embodiments the invention relates to a first polypeptide having lipase activity wherein said polypeptide is a polypeptide having at least one of: (a) a lipase activity (LU) relative to the absorbance at 280 nm (A280) of less than 500, less than 450, less than 400, less than 350, less than 300, less than 250, less than 200, less than 150, less than 100 or less than 50 LU/A280, in which one unit of LU (1 LU) is defined as the amount of enzyme capable of releasing 1 micro mol of butyric acid per minute at 30° C. at pH 7, and the absorbance of the polypeptide is measured at 280 nm; (b) a Risk performance odor (R) below 0.5, below 0.4, below 0.3, below 0.2, below 0.1, or below 0.05, in which R is calculated as the ratio between the amount butyric acid released from a polypeptide washed swatch and the amount butyric acid released from a reference polypeptide washed swatch, after both values have been corrected for the amount of butyric acid released from a non-polypeptide washed swatch; or (c) a Benefit Risk factor (BR) of at least 1.8, at least 1.9, at least 2.0, at least 2.5, at least 3.0, at least 4.0, at least 5.0, or at least 6.0 in which BR is defined as the average wash performance ($RP_{avg}$) divided with the risk performance odor (R).

In some embodiments the invention relates to the first polypeptide wherein said polypeptide comprises alterations of the amino acids at the positions T231R+N233R+I255A+P256K and at least one of (a) S58A+V60S+A150G+L227G; or (b) E210V/G; which positions are corresponding to SEQ ID NO: 2.

In some embodiments the invention relates to the first polypeptide further comprising at least one of the alteration of the amino acid at the positions I86V or T143S.

In some embodiments the invention relates to the first polypeptide, wherein the polypeptide comprises at least one further alteration selected from a substitution, a deletion or an addition of at least one amino acid at a position corresponding to position E1, D27, N33, S83, G91, N94, K98, E99, D102, D111N, G163K, I202L, E210, S216, L259 or L269 of SEQ ID NO: 2.

In some embodiments the invention relates to the first polypeptide, wherein the at least one alteration is selected from the group consisting of: E1N/*, D27N, N33Q, S83T, G91N, N94R, K98I, E99K, D102A, D111N, G163K, I202L, E210A, S216P, L259F, or L269APIA of SEQ ID NO: 2.

In some embodiments the invention relates to a second polypeptide comprising alterations of the amino acids at the positions T231R+N233R+I255A+P256K and at least one of: (a) S58A+V60S+A150G+L227G; or (b) E210V/G; which positions are corresponding to SEQ ID NO: 2.

In some embodiments the invention relates to the second polypeptide further comprising at least one of the alterations of the amino acid at the positions I86V or T143S.

In some embodiments the invention relates to the second polypeptide, wherein the polypeptide comprises at least one further alteration selected from a substitution, a deletion or an addition of at least one amino acid at a position corresponding to position E1, D27, N33, S83, G91, N94, K98I, E99, D102, D111, G163, I202, E210, S216, L259 or L269 of SEQ ID NO: 2.

In some embodiments the invention relates to the second polypeptide, wherein the at least one alteration is selected from the group consisting of: E1N/*, D27N, N33Q, S83T, G91N, N94R, K98I, E99K, D102A, D111N, G163K, I202L, E210A, S216P, L259F, or L269APIA of SEQ ID NO: 2.

In some embodiments the invention relates to the first polypeptide, wherein said polypeptide comprises alterations selected from the group consisting of: (a) T231R+N233R+L269APIA; (b) S58T+V60K+A150G+T231R+N233I+D234G; (c) S58T+V60K+I86V+D102A+A150G+L227G+T231R+N233R+P256K; (d) S58N+V60S+I86P+T231R+N233R+P256S; (e) S58N+V60S+I86S+L227G+T231R+N233R+P256S; and (f) S58N+V60S+I86T+L227G+T231R+N233R+P256L.

In some embodiments the invention relates to the first or the second polypeptide, wherein said polypeptide comprises alterations selected from the group consisting of: (a) S58A+ V60S+S83T+A150G+L227G+T231R+N233R+I255A+ P256K; (b) S58A+V60S+I86V+A150G+L227G+T231R+ N233R+I255A+P256K; (c) S58A+V60S+I86V+T143S+ A150G+L227G+T231R+N233R+I255A+P256K; (d) S58A+V60S+I86V+T143S+A150G+G163K+S216P+ L227G+T231R+N233R+I255A+P256K; (e) E1*+S58A+ V60S+I86V+T143S+A150G+L227G+T231R+N233R+ I255A+P256K; (f) S58A+V60S+I86V+K98I+E99K+ E1L+D27K+V60K+I86V+A150G+S219P+L227G+ T231R+N233R+P256K; (r) E1N+S58A+V60S+S83T+ A150G+L227G+T231R+N233R+I255A+P256K; (s) E1N+ S58T+V60K+I86V+D102A+T143S+A150G+L227G+ T231R+N233R+I255A+P256K; (t) E1N+S58A+V60S+ I86V+K98I+E99K+D102A+T143S+A150G+S216P+ L227G+T231R+N233R+I255A+P256K; and (u) S58A+ V60S+S83T+A150A+L227G+T231R+N233R+I255A+ P256K.

TABLE 1

Alterations that may be comprised in the polypeptides

| Polypeptide | Mutations in SEQ ID NO: 2 |
|---|---|
| 1 | T231R + N233R + L269APIA |
| 2 | S58T + V60K + A150G + T231R + N233I + D234G |
| 3 | S58T + V60K + I86V + D102A + A150G + L227G + T231R + N233R + P256K |
| 4 | S58N + V60S + I86P + T231R + N233R + P256S |
| 5 | S58N + V60S + I86S + L227G + T231R + N233R + P256S |
| 6 | S58N + V60S + I86T + L227G + T231R + N233R + P256L |
| 7 | S58A + V60S + S83T + A150G + L227G + T231R + N233R + I255A + P256K |
| 8 | S58A + V60S + I86V + A150G + L227G + T231R + N233R + I255A + P256K |
| 9 | S58A + V60S + I86V + T143S + A150G + L227G + T231R + N233R + I255A + P256K |
| 10 | S58A + V60S + I86V + T143S + A150G + G163K + S216P + L227G + T231R + N233R + I255A + P256K |
| 11 | E1* + S58A + V60S + I86V + T143S + A150G + L227G + T231R + N233R + I255A + P256K |
| 12 | S58A + V60S + I86V + K98I + E99K + T143S + A150G + L227G + T231R + N233R + I255A + P256K |
| 13 | E1N, S58A, V60S, I86V, K98I, E99K, T143S, A150G, L227G, T231R, N233R, I255A, P256K, L259F |
| 14 | S58A, V60S, I86V, K98I, E99K, D102A, T143S, A150G, L227G, T231R, N233R, I255A, P256K |
| 15 | N33Q, S58A, V60S, I86V, T143S, A150G, L227G, T231R, N233R, I255A, P256K |
| 16 | E1* + S58A + V60S + I86V + K98I + E99K, T143S + A150G + L227G + T231R + N233R + I255A + P256K |
| 17 | E1N + S58A + V60S + I86V + K98I + E99K + T143S + A150G + S216P + L227G + T231R + N233R + I255A + P256K |
| 18 | D27N + S58A + V60S + I86V + G91N + N94R + D111N + T143S + A150G + L227G + T231R + N233R + I255A + P256K |
| 19 | E1N + S58A + V60S + I86V + K98I + E99K + T143S + A150G + E210A + S216P + L227G + T231R + N233R + I255A + P256K |
| 20 | A150G + E210V + T231R + N233R + I255A + P256K |
| 21 | I202L + E210G + T231R + N233R + I255A + P256K |
| 22 | E1N + A18K + V60K + I86V + A150G + E210A + L227G + T231R + N233R + P256K |
| 23 | E1L + D27K + V60K + I86V + A150G + S219P + L227G + T231R + N233R + P256K |
| 24 | E1N + S58A + V60S + S83T + A150G + L227G + T231R + N233R + I255A + P256K |
| 25 | E1N + S58T + V60K + I86V + D102A + T143S + A150G + L227G + T231R + N233R + I255A + P256K |
| 26 | E1N + S58A + V60S + I86V + K98I + E99K + D102A + T143S + A150G + S216P + L227G + T231R + N233R + I255A + P256K |
| 27 | S58A + V60S + S83T + A150A + L227G + T231R + N233R + I255A + P256K |

T143S+A150G+L227G+T231R+N233R+I255A+P256K; (g) E1N+S58A+V60S+I86V+K98I+E99K+T143S+ A150G+L227G+T231R+N233R+I255A+P256K+L259F; (h) S58A+V60S+I86V+K98I+E99K+D102A+T143S+ A150G+L227G+T231R+N233R+I255A+P256K; (i) N33Q+S58A+V60S+I86V+T143S+A150G+L227G+ T231R+N233R+I255A+P256K; (j) E1*+S58A+V60S+ I86V+K98I+E99K+T143S+A150G+L227G+T231R+ N233R+I255A+P256K; (k) E1N+S58A+V60S+I86V+ K98I+E99K+T143S+A150G+S216P+L227G+T231R+ N233R+I255A+P256K; (l) D27N+S58A+V60S+I86V+ G91N+N94R+D111N+T143S+A150G+L227G+T231R+ N233R+I255A+P256K; (m) E1N+S58A+V60S+I86V+ K98I+E99K+T143S+A150G+E210A+S216P+L227G+ T231R+N233R+I255A+P256K; (n) A150G+E210V+ T231R+N233R+I255A+P256K; (o) I202L+E210G+ T231R+N233R+I255A+P256K; (p) E1N+A18K+V60K+ I86V+A150G+E210A+L227G+T231R+N233R+P256K; (q)

In some embodiments the invention relates to a first polypeptide, wherein said polypeptide comprises alterations selected from the group consisting of: (a) T231R+N233R+ L269APIA; (b) S58T+V60K+A150G+T231R+N233I+ D234G; (c) S58T+V60K+I86V+D102A+A150G+L227G+ T231R+N233R+P256K; (d) S58N+V60S+I86P+T231R+ N233R+P256S; (e) S58N+V60S+I86S+L227G+T231R+ N233R+P256S; and (f) S58N+V60S+I86T+L227G+ T231R+N233R+P256L.

In some embodiments the invention relates to a first or a second polypeptide, wherein said polypeptide comprises alterations selected from the group consisting of: (a) S58A+ V60S+S83T+A150G+L227G+T231R+N233R+I255A+ P256K; (b) S58A+V60S+I86V+A150G+L227G+T231R+ N233R+I255A+P256K; (c) S58A+V60S+I86V+T143S+ A150G+L227G+T231R+N233R+I255A+P256K; (d) S58A+V60S+I86V+T143S+A150G+G163K+S216P+ L227G+T231R+N233R+I255A+P256K; (e) E1*+S58A+

V60S+I86V+T143S+A150G+L227G+T231R+N233R+ I255A+P256K; (f) S58A+V60S+I86V+K98I+E99K+ T143S+A150G+L227G+T231R+N233R+I255A+P256K; (g) E1N+S58A+V60S+I86V+K98I+E99K+T143S+ A150G+L227G+T231R+N233R+I255A+P256K+L259F; (h) S58A+V60S+I86V+K98I+E99K+D102A+T143S+ A150G+L227G+T231R+N233R+I255A+P256K; (i) N33Q+S58A+V60S+I86V+T143S+A150G+L227G+ T231R+N233R+I255A+P256K; (j) E1*+S58A+V60S+ I86V+K98I+E99K+T143S+A150G+L227G+T231R+ N233R+I255A+P256K; (k) E1N+S58A+V60S+I86V+ K98I+E99K+T143S+A150G+S216P+L227G+T231R+ N233R+I255A+P256K; (l) D27N+S58A+V60S+I86V+ G91N+N94R+D111N+T143S+A150G+L227G+T231R+ N233R+I255A+P256K; (m) E1N+S58A+V60S+I86V+ K98I+E99K+T143S+A150G+E210A+S216P+L227G+ T231R+N233R+I255A+P256K; (n) A150G+E210V+ T231R+N233R+I255A+P256K; (o) I202L+E210G+ T231R+N233R+I255A+P256K; (p) E1N+A18K+V60K+ I86V+A150G+E210A+L227G+T231R+N233R+P256K; (q) E1L+D27K+V60K+I86V+A150G+S219P+L227G+ T231R+N233R+P256K; (r) E1N+S58A+V60S+S83T+ A150G+L227G+T231R+N233R+I255A+P256K; (s) E1N+ S58T+V60K+I86V+D102A+T143S+A150G+L227G+ T231R+N233R+I255A+P256K; (t) E1N+S58A+V60S+ I86V+K98I+E99K+D102A+T143S+A150G+S216P+ L227G+T231R+N233R+I255A+P256K; and (u) S58A+ V60S+S83T+A150A+L227G+T231R+N233R+I255A+ P256K.

Polynucleotides, Expression Vector, Host Cell, Production of Polypeptides

In some embodiments the invention relates to an isolated polynucleotide encoding the polypeptide. Such polynucleotides may hybridize under very low stringency conditions, preferably low stringency conditions, more preferably medium stringency conditions, more preferably medium-high stringency conditions, even more preferably high stringency conditions, and most preferably very high stringency conditions with (i) nucleotides 178 to 660 of SEQ ID NO: 1, (ii) the cDNA sequence contained in nucleotides 178 to 660 of SEQ ID NO: 1, (iii) a subsequence of (i) or (ii), or (iv) a complementary strand of (i), (ii), or (iii) (J. Sambrook, E. F. Fritsch, and T. Maniatus, 1989, Molecular Cloning, A Laboratory Manual, 2d edition, Cold Spring Harbor, N.Y.). A subsequence of SEQ ID NO: 1 contains at least 100 contiguous nucleotides or preferably at least 200 contiguous nucleotides. Moreover, the subsequence may encode a polypeptide fragment which has lipase activity.

For long probes of at least 100 nucleotides in length, very low to very high stringency conditions are defined as prehybridization and hybridization at 42° C. in 5×SSPE, 0.3% SDS, 200 ug/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

In some embodiments the invention relates to a nucleic acid construct comprising the polynucleotide operationally linked to at least one control sequence that directs the production of the polypeptide in an expression host.

In some embodiments the invention relates to a recombinant expression vector comprising the nucleic acid construct.

In some embodiments the invention relates to a transformed host cell comprising the nucleic acid construct or the recombinant expression vector.

The isolated polynucleotide encoding the polynucleotide, the nucleic acid construct comprising the polynucleotide, the recombinant expression vector comprising the nucleic acid construct, and the transformed host cell comprising the nucleic acid construct or the recombinant expression vector may all be obtained by methods known in the art.

In some embodiments the invention relates to a method of preparing the polypeptide comprising the steps: (a) cultivating the transformed host cell comprising the nucleic acid construct or the recombinant expression vector comprising the nucleotide acid construct under conditions conductive for the production of the polypeptide; and (b) recovering the polypeptide. The method may be practiced according to principles known in the art.

Uses

Enzymes of the present invention may be used, incl. industrial use for removing of fatty matter.

In some embodiments the invention relates to a formulation comprising the polypeptide. In further embodiments the invention relates to a formulation, wherein said formulation may be a solid or a liquid formulation. The polypeptide may be used both in a solid as well as in a liquid formulation.

In some embodiments the invention relates to a method of reducing the formation of odor generating short chain fatty acids during lipid hydrolysis by employing the polypeptide.

EXAMPLES

The present invention is further described by the following examples which should not be construed as limiting the scope of the invention.

Chemicals used as buffers and substrates were commercial products of at least reagent grade.

Example 1

Production of Lipase Variants

A plasmid containing the gene encoding the polypeptide is constructed and transformed into a suitable host cell using standard methods of the art.

Fermentation is carried out as a fed-batch fermentation using a constant medium temperature of 34° C. and a start volume of 1.2 liter. The initial pH of the medium is set to 6.5. Once the pH has increased to 7.0 this value is maintained through addition of 10% $H_3PO_4$. The level of dissolved oxygen in the medium is controlled by varying the agitation rate and using a fixed aeration rate of 1.0 liter air per liter medium per minute. The feed addition rate is maintained at a constant level during the entire fed-batch phase.

The batch medium contains maltose syrup as carbon source, urea and yeast extract as nitrogen source and a mixture of trace metals and salts. The feed added continuously during the fed-batch phase contains maltose syrup as carbon source whereas yeast extract and urea is added in order to assure a sufficient supply of nitrogen.

Purification of the polypeptide may be done by use of standard methods known in the art, e.g. by filtering the fermentation supernatant and subsequent hydrophobic chromatography and ion exchange chromatography, e.g. as described in EP 0 851 913 EP, Example 3.

Example 2

Lipase Activity Unit (LU) Relative to Absorbance at 280 nm (LU/A280)

The activity of the lipase (LU) is determined as described above in the section Lipase activity. The absorbance of the lipase at 280 nm is measured (A280). The specific activity of a polypeptide may be expressed as the ratio of LU/A280.

The relative LU/A280 is calculated as the LU/A280 of the polypeptide divided by the LU/A280 of a reference enzyme. In the context of the present invention the reference enzyme is the lipase of SEQ ID NO:2 with the substitutions T231R+N233R.

Example 3

Calculation of the Relative Performance (RP) from Data Obtained from the Automated Mechanical Stress Assay (AMSA)

Polypeptides of the present invention are tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24. The containers, which contain the detergent test solution, consist of cylindrical holes (6 mm diameter, 10 mm depth) in a metal plate. The stained fabric (test material) lies on the top of the metal plate and is used as a lid and seal on the containers. Another metal plate lies on the top of the stained fabric to avoid any spillage from each container. The two metal plates together with the stained fabric are vibrated up and down at a frequency of 30 Hz with an amplitude of 2 mm.

TABLE 2

The experimental conditions for AMSA

| | Ingredient | % wt |
|---|---|---|
| Test solution | Sodium alkyl ether sulphate (Surfac LC70) | 12.0 |
| | Alkylbenzenesulfonate (LAS) | 7.0 |
| | Soap Tallow/Coconut 80/20 | 3.2 |
| | Alcohol ethoxylate (Neodol 23-9) | 2.4 |
| | Alkyl dimethylamine oxide (Empigen OB) | 2.0 |
| | Citric acid (sodium) | 2.8 |
| | Sodium hydroxide | 1.6 |
| | Glycerin | 2.3 |
| | Monoethanolamine | 2.7 |
| | Monopropylenglycol (MPG) | 4.7 |
| | Water | 59.2 |
| Test solution volume | 160 micro l | |
| pH | As is (~8.3), adjusted with Sodium hydroxide and Citric acid | |
| Wash time | 20 minutes | |
| Temperature | 30° C. | |
| Water hardness | 6° dH Ratio of $Ca^{2+}/Mg^{2+}/NaHCO_3$: 2:1:4.5 | |

TABLE 2-continued

The experimental conditions for AMSA

| | Ingredient | % wt |
|---|---|---|
| Enzyme concentration in test solution | 0.125, 0.25, 0.50, 0.50 mg ep/l | |
| Drying | Performance: After washing the textile pieces (coffee cream turmeric) are immediately flushed in tap water and air-dried at 85° C. in 5 min. Odor: After washing the textile pieces (cream turmeric) are immediately flushed in tap water and dried at room temperature (20° C.) for 2 hours | |
| Test material | Cream turmeric swatch or coffee cream turmeric swatch as described below (EMPA221 used as cotton textile obtained from EMPA St. Gallen, Lerchfeldstrasse 5, CH-9014 St. Gallen, Switzerland) | |

Cream-turmeric swatches and coffee cream turmeric swatches were prepared by mixing 5 g of turmeric (Santa Maria, Denmark) with 10 g cream (38% fat, Arla, Denmark) and 100 g coffee cream (9% fat, Arla, Denmark) at 50° C., respectively. The mixture was left at this temperature for about 20 minutes and filtered (50° C.) to remove any undissolved particles. The mixture was cooled to 20° C. and woven cotton swatches, EMPA221, were immersed in the cream-turmeric mixture and afterwards allowed to dry at room temperature over night and frozen until use. The preparation of cream-turmeric swatches is disclosed in WO 06125437.

The performance of the polypeptide was measured as the brightness of the color of the textile samples washed with that specific polypeptide. Brightness can also be expressed as the intensity of the light reflected from the textile sample when illuminated with white light. When the textile is stained the intensity of the reflected light is lower, than that of a clean textile. Therefore the intensity of the reflected light can be used to measure wash performance of a polypeptide variant.

Color measurements were made with a professional flatbed scanner (PFU DL2400pro), which is used to capture an image of the washed textile samples. The scans were made with a resolution of 200 dpi and with an output color depth of 24 bits. In order to get accurate results, the scanner was frequently calibrated with a Kodak reflective IT8 target.

To extract a value for the light intensity from the scanned images, a special designed software application was used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int=\sqrt{r^2+g^2+b^2}$$

The wash performance (P) of the polypeptides was calculated in accordance with the formula:

$$P=Int(v)-Int(r),$$

where Int(v) is the light intensity value of textile surface washed with enzyme, and Int(r) is the light intensity value of textile surface washed without enzyme.

A relative performance score is given as the result of the AMSA wash in accordance with the definition: Relative Performance scores (RP) are summing up the performances (P) of the tested polypeptide against the reference polypeptide:

$$RP=P(\text{test polypeptide})/P(\text{reference polypeptide}).$$

RP$_{avg}$ indicates the average relative performance compared to the reference polypeptide of measurements done at 0.5 mg ep/l.

A polypeptide is considered to exhibit improved wash performance, if it performs better than the reference. In the context of the present invention the reference enzyme is the lipase of SEQ ID NO:2 with the substitutions T231R+ N233R.

Example 4

Calculation of Risk Factor (R) from Solid Phase Micro Extraction Gas Chromatograph Measurements The butyric acid release from the lipase washed swatches were measured by Solid Phase Micro Extraction Gas Chromatography (SPME-GC) using the following method. Four pieces of textiles (5 mm in diameter), washed in the specified solution in Table 2 containing 0.5 mg/l lipase, were transferred to a Gas Chromatograph (GC) vial. The samples were incubated at 30° C. for 24 h and subsequently heated to 140° C. for 30 min and stored at 20° C.-25° C. for at least 4 h before analysis. The analysis was performed on a Varian 3800 GC equipped with a Stabilwax-DA w/Integra-Guard column (30 m, 0.32 mm ID and 0.25 micro-m df) and a Carboxen PDMS SPME fibre (85 micro-m). Sampling from each GC vial was done at 50° C. for 8 min with the SPME fibre in the headspace over the textile pieces and the sampled compounds were subsequently injected onto the column (injector temperature=250° C.). Column flow=2 ml Helium/min. Column oven temperature gradient: 0 min=50° C., 2 min=50° C., 6 min 45 s=240° C., 11 min 45 s=240° C. Detection was done using a Flame Ionization Detector (FID) and the retention time for butyric acid was identified using an authentic standard.

The risk performance odor (R) of a polypeptide is the ratio between the amount butyric acid released (peak area) from a polypeptide washed swatch and the amount butyric acid released (peak area) from a reference polypeptide washed swatch, after both values have been corrected for the amount of butyric acid released (peak area) from a non-polypeptide washed swatch (blank). The reference polypeptide is the polypeptide of SEQ ID NO: 2 with the substitutions T231R+ N233R. The risk performance odor (R) of the polypeptide is calculated in accordance with the below formula:

Odor=measured butyric acid (peak area) released from the textile surface.

$\alpha_{test\ enzyme} = Odor_{test\ enzyme} - Odor_{blank}$ $\alpha_{reference\ enzyme} = Odor_{reference\ enzyme} - Odor_{blank}$ $R = \alpha_{test\ enzyme} / \alpha_{reference\ enzyme}$ A polypeptide is considered to exhibit reduced odor compared to the reference if the R factor is lower than 1.

Example 5

Benefit Risk Factor (BR)

The Benefit Risk factor describing the wash performance compared to the reduced risk for odor is thus defined as:

$BR = RP_{avg}/R$

A variant is considered to exhibit improved wash performance and reduced odor, if the BR factor is higher than 1.

TABLE 3

Specific activity (LU/A280), risk performance odor (R) and Benefit Risk factor (BR) for some polypeptides of the invention

| Polypeptide | Mutations in SEQ ID NO: 2 | LU/A280 Ex. 2 | R Ex. 4 | BR Ex. 5 |
|---|---|---|---|---|
| REF | T231R + N233R | 4760 | 1.00 | 1.00 |
| 1 | T231R + N233R + L269APIA | 127 | 0.19 | 2.77 |
| 2 | S58T + V60K + A150G + T231R + N233I + D234G | 1287 | 0.51 | 2.02 |
| 3 | S58T + V60K + I86V + D102A + A150G + L227G + T231R + N233R + P256K | 358 | 0.44 | 2.04 |
| 4 | S58N + V60S + I86P + T231R + N233R + P256S | ND | 0.5 | 2 |
| 5 | S58N + V60S + I86S + L227G + T231R + N233R + P256S | ND | 0.2 | 2.82 |
| 6 | S58N + V60S + I86T + L227G + T231R + N233R + P256L | 1576 | 0.34 | 2.11 |
| 7 | S58A + V60S + S83T + A150G + L227G + T231R + N233R + I255A + P256K | 141 | 0.12 | 2.88 |
| 8 | S58A + V60S + I86V + A150G + L227G + T231R + N233R + I255A + P256K | 479 | 0.20 | 3.04 |
| 9 | S58A + V60S + I86V + T143S + A150G + L227G + T231R + N233R + I255A + P256K | 232 | 0.06 | 6.20 |
| 10 | S58A + V60S + I86V + T143S + A150G + G163K + S216P + L227G + T231R + N233R + I255A + P256K | 208 | 0.09 | 4.54 |
| 11 | E1* + S58A + V60S + I86V + T143S + A150G + L227G + T231R + N233R + I255A + P256K | 273 | 0.27 | 2.87 |
| 12 | S58A + V60S + I86V + K98I + E99K + T143S + A150G + L227G + T231R + N233R + I255A + P256K | 143 | 0.20 | 3.12 |
| 13 | E1N, S58A, V60S, I86V, K98I, E99K, T143S, A150G, L227G, T231R, N233R, I255A, P256K, L259F | ND | 0.10 | 5.20 |
| 14 | S58A, V60S, I86V, K98I, E99K, D102A, T143S, A150G, L227G, T231R, N233R, I255A, P256K | 15 | 0.16 | 3.87 |
| 15 | N33Q, S58A, V60S, I86V, T143S, A150G, L227G, T231R, N233R, I255A, P256K | 394 | 0.09 | 6.55 |

TABLE 3-continued

Specific activity (LU/A280), risk performance odor (R) and Benefit Risk factor (BR) for some polypeptides of the invention

| Polypeptide | Mutations in SEQ ID NO: 2 | LU/A280 Ex. 2 | R Ex. 4 | BR Ex. 5 |
|---|---|---|---|---|
| 16 | E1* + S58A + V60S + I86V + K98I + E99K, T143S + A150G + L227G + T231R + N233R + I255A + P256K | 129 | 0.23 | 3.02 |
| 17 | E1N + S58A + V60S + I86V + K98I + E99K + T143S + A150G + S216P + L227G + T231R + N233R + I255A + P256K | 123 | 0.22 | 3.17 |
| 18 | D27N + S58A + V60S + I86V + G91N + N94R + D111N + T143S + A150G + L227G + T231R + N233R + I255A + P256K | 946 | 0.25 | 2.70 |
| 19 | E1N + S58A + V60S + I86V + K98I + E99K + T143S + A150G + E210A + S216P + L227G + T231R + N233R + I255A + P256K | 127 | 0.28 | 2.83 |
| 20 | A150G + E210V + T231R + N233R + I255A + P256K | 666 | 0.45 | 1.99 |
| 21 | I202L + E210G + T231R + N233R + I255A + P256K | 1062 | 0.37 | 2.33 |
| 22 | E1N + A18K + V60K + I86V + A150G + E210A + L227G + T231R + N233R + P256K | 107 | 0.30 | 2.6 |
| 23 | E1L + D27K + V60K + I86V + A150G + S219P + L227G + T231R + N233R + P256K | 488 | 0.22 | 2.8 |
| 24 | E1N + S58A + V60S + S83T + A150G + L227G + T231R + N233R + I255A + P256K | 98 | 0.15 | 2.4 |
| 25 | E1N + S58T + V60K + I86V + D102A + T143S + A150G + L227G + T231R + N233R + I255A + P256K | 144 | 0.28 | 2.3 |
| 26 | E1N + S58A + V60S + I86V + K98I + E99K + D102A + T143S + A150G + S216P + L227G + T231R + N233R + I255A + P256K | 14 | 0.31 | 2.1 |
| 27 | S58A + V60S + S83T + A150A + L227G + T231R + N233R + I255A + P256K | 280 | 0.18 | 1.9 |

The invention claimed is:

1. An isolated polypeptide having lipase activity wherein said polypeptide is at least 80% identical to SEQ ID NO:2 and is a polypeptide having at least one of:
   a lipase activity (LU) relative to the absorbance at 280 nm (A280) of less than 500 LU/A280, in which one unit of LU (1 LU) is defined as the amount of enzyme capable of releasing 1 micro mol of butyric acid per minute at 30° C. at pH 7, and the absorbance of the polypeptide is measured at 280 nm;
   a Risk performance odor (R) below 0.1, in which R is calculated as the ratio between the amount of butyric acid released from a polypeptide washed swatch and the amount of butyric acid released from a reference polypeptide washed swatch, after both values have been corrected for the amount of butyric acid released from a non-polypeptide washed swatch; or
   a Benefit Risk factor (BR) of at least 1.8, in which BR is defined as the average wash performance ($RP_{avg}$) divided with the risk performance odor (R); and
wherein said polypeptide comprises alterations of the amino acids at positions T231R+N233R+I255A+P256K and at least one of:
   S58A+V60S+A150G+L227G; or
   E210V/G;
which positions correspond to SEQ ID NO:2.

2. The polypeptide of claim 1 further comprising at least one of the alteration of the amino acid at the positions I86V or T143S.

3. The polypeptide of claim 1, wherein the polypeptide comprises at least one further alteration selected from a substitution, a deletion or an addition of at least one amino acid at a position corresponding to position E1, D27, N33, S83, G91, N94, K98, E99, D102, D111, G163, I202, E210, S216, L259 or L269 of SEQ ID NO:2.

4. The polypeptide of claim 3, wherein the at least one alteration is selected from the group consisting of: E1N, E1*, D27N, N33Q, S83T, G91N, N94R, K98I, E99K, D102A, D111N, G163K, I202L, E210A, S216P, L259F, or L269APIA of SEQ ID NO: 2.

5. The polypeptide of claim 1, further comprising at least one of the alteration of the amino acid at the positions I86V or T143S.

6. The polypeptide of claim 1, wherein said polypeptide comprises at least one further alteration selected from a substitution, a deletion or an addition of at least one amino acid at a position corresponding to position E1, D27, N33, S83, G91, N94, K98, E99, D102, D111, G163, I202, E210, S216, L259 or L269 of SEQ ID NO:2.

7. The polypeptide of claim 6, wherein the at least one alteration is selected from the group consisting of: E1N, E1*, D27N, N33Q, S83T, G91N, N94R, K98I, E99K, D102A, D111N, G163K, I202L, E210A, S216P, L259F, or L269APIA of SEQ ID NO:2.

8. An isolated polypeptide having lipase activity wherein said polypeptide is at least 80% identical to SEQ ID NO:2 and is a polypeptide having at least one of
   a lipase activity (LU) relative to the absorbance at 280 nm (A280) of less than 500 LU/A280, in which one unit of LU (1 LU) is defined as the amount of enzyme capable of releasing 1 micro mol of butyric acid per minute at 30° C. at pH 7, and the absorbance of the polypeptide is measured at 280 nm;
   a Risk performance odor (R) below 0.1, in which R is calculated as the ratio between the amount of butyric acid released from a polypeptide washed swatch and the amount of butyric acid released from a reference polypeptide washed swatch, after both values have been corrected for the amount of butyric acid released from a non-polypeptide washed swatch; or
   a Benefit Risk factor (BR) of at least 1.8, in which BR is defined as the average wash performance ($RP_{avg}$) divided with the risk performance odor (R); and
wherein said polypeptide comprises alterations selected from the group consisting of:
T231R+N233R+L269APIA;
S58T+V60K+A150G+T231R+N233I+D234G;
S58T+V60K+I86V+D102A+A150G+L227G+T231R+N233R+P256K;
S58N+V60S+I86P+T231R+N233R+P256S;
S58N+V60S+I86S+L227G+T231R+N233R+P256S; and
S58N+V60S+I86T+L227G+T231R+N233R+P256L.

9. An isolated polypeptide having lipase activity wherein said polypeptide is at least 80% identical to SEQ ID NO:2 and is a polypeptide having at least one of
   a lipase activity (LU) relative to the absorbance at 280 nm (A280) of less than 500 LU/A280, in which one unit of LU (1 LU) is defined as the amount of enzyme capable of releasing 1 micro mol of butyric acid per minute at 30° C. at pH 7, and the absorbance of the polypeptide is measured at 280 nm;
   a Risk performance odor (R) below 0.1, in which R is calculated as the ratio between the amount of butyric acid released from a polypeptide washed swatch and the amount of butyric acid released from a reference polypeptide washed swatch, after both values have been corrected for the amount of butyric acid released from a non-polypeptide washed swatch; or
   a Benefit Risk factor (BR) of at least 1.8, in which BR is defined as the average wash performance ($RP_{avg}$) divided with the risk performance odor (R); and
wherein said polypeptide comprises alterations selected from the group consisting of:
S58A+V60S+I83T+A150G+L227G+T231R+N233R+I255A+P256K;
S58A+V60S+I86V+A150G+L227G+T231R+N233R+I255A+P256K;
S58A+V60S+I86V+T143S+A150G+L227G+T231R+N233R+I255A+P256K;
S58A+V60S+I86V+T143S+A150G+G163K+S216P+L227G+T231R+N233R+I255A+P256K;
E1*+S58A+V60S+I86V+T143S+A150G+L227G+T231R+N233R+I255A+P256K;
S58A+V60S+I86V+K98I+E99K+T143S+A150G+L227G+T231R+N233R+I255A+P256K;
E1N+S58A+V60S+I86V+K98I+E99K+T143S+A150G+L227G+T231R+N233R+I255A+P256K+L259F;
S58A+V60S+I86V+K98I+E99K+D102A+T143S+A150G+L227G+T231R+N233R+I255A+P256K;
N33Q+S58A+V60S+I86V+T143S+A150G+L227G+T231R+N233R+I255A+P256K;
E1*+S58A+V60S+I86V+K98I+E99K+T143S+A150G+L227G+T231R+N233R+I255A+P256K;
E1N+S58A+V60S+I86V+K98I+E99K+T143S+A150G+S216P+L227G+T231R+N233R+I255A+P256K;
D27N+S58A+V60S+I86V+G91N+N94R+D111N+T143S+A150G+L227G+T231R+N233R+I255A+P256K;
E1N+S58A+V60S+I86V+K98I+E99K+T143S+A150G+E210A+S216P+L227G+T231R+N233R+I255A+P256K;
A150G+E210V+T231R+N233R+I255A+P256K;
I202L+E210G+T231R+N233R+I255A+P256K;
E1N+A18K+V60K+I86V+A150G+E210A+L227G+T231R+N233R+P256K;

E1L+D27K+V60K+I86V+A150G+S219P+L227G+ T231R+N233R+P256K;
E1N+S58A+V60S+S83T+A150G+L227G+T231R+ N233R+I255A+P256K;
E1N+S58T+V60K+I86V+D102A+T143S+A150G+ L227G+T231R+N233R+I255A+P256K;
E1N+S58A+V60S+I86V+K98I+E99K+D102A+T143S+ A150G+S216P+L227G+T231R+N233R+I255A+P256K; and
S58A+V60S+S83T+A150A+L227G+T231R+N233R+ I255A+P256K.

10. The isolated polypeptide of claim 1, wherein said polypeptide is at least 85% identical to SEQ ID NO:2.

11. A formulation comprising the polypeptide of claim 1.

12. The formulation of claim 11, wherein said formulation may be a solid or a liquid formulation.

13. A method of reducing the formation of odor generating short chain fatty acids during lipid hydrolysis comprising contacting a lipid with the polypeptide of claim 1.

14. The isolated polypeptide of claim 1, wherein said polypeptide is at least 90% identical to SEQ ID NO:2.

15. The isolated polypeptide of claim 1, wherein said polypeptide is at least 95% identical to SEQ ID NO:2.

16. The isolated polypeptide of claim 1, wherein said polypeptide is at least 96% identical to SEQ ID NO:2.

17. The isolated polypeptide of claim 1, wherein said polypeptide is at least 97% identical to SEQ ID NO:2.

18. The isolated polypeptide of claim 1, wherein said polypeptide is at least 98% identical to SEQ ID NO:2.

* * * * *